United States Patent [19]

Hyatt

[11] 4,018,832

[45] Apr. 19, 1977

[54] NOVEL COMPLEXING AGENTS DERIVED FROM CYCLOTRIVERATRYLENE

[75] Inventor: John A. Hyatt, Kingsport, Tenn.

[73] Assignee: Eastman Kodak Company, Rochester, N.Y.

[22] Filed: July 14, 1976

[21] Appl. No.: 705,193

[52] U.S. Cl. .................... 260/613 B; 260/613 R; 252/364; 260/465 R; 260/488 CD; 260/669 QZ

[51] Int. Cl.[2] .................... C07C 43/26

[58] Field of Search .................... 260/613 R, 613 B

[56] References Cited

UNITED STATES PATENTS 3,830,850 8/1974 Stratton .................... 260/613 B

OTHER PUBLICATIONS

Lindsey, Journal Chemical Society (London)(1965) pp. 1685–1692.

*Primary Examiner*—Bernard Helfin

*Attorney, Agent, or Firm*—Elliott Stern; Daniel B. Reece, III

[57] ABSTRACT

Compounds having the formula wherein R is $-(CH_2-CH_2-O)_n-R^1$, $n$ is an integer of 1 to 5 and $R^1$ is alkyl of 1 to 6 carbon atoms. These compounds are useful as complexing agents which solubilize certain usually insoluble inorganic compounds and salts of organic compounds in organic solvents, and as catalysts in certain organic synthetic reactions.

5 Claims, No Drawings

NOVEL COMPLEXING AGENTS DERIVED FROM CYCLOTRIVERATRYLENE

This invention relates to compositions of matter which are useful in rendering normally insoluble inorganic materials soluble in certain organic solvents. These compounds are characterized by the structure I

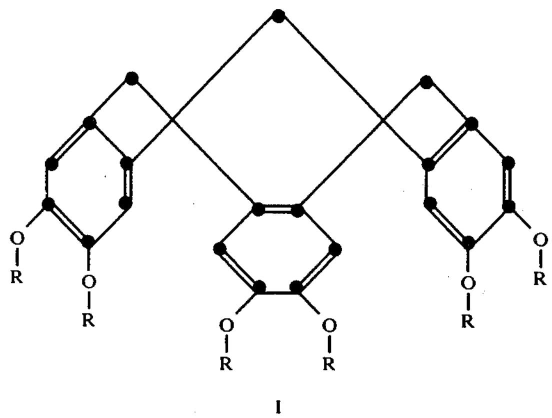

I wherein R is $-(CH_2CH_2-O)_nR^1$, $n$ is an integer of 1 to 5 and $R^1$ is alkyl of 1 to 6 carbon atoms and preferably methyl, ethyl, or butyl.

Compounds of the above structure are prepared by reacting cyclotriveratrylene II with ethylene glycol derivatives such as ethylene glycol monomethyl ether p-toluenesulfonate, diethylene glycol monomethyl ether p-toluenesulfonate, diethylene glycol monoethyl ether p-toluene-sulfonate, triethylene glycol monoethyl ether p-toluenesulfonate, tetraethylene glycol monomethyl ether p-toluenesulfonate, diethylene glycol monobutyl ether methanesulfonate, 2-(2-methoxy)ethoxybromoethane, 2(2-ethoxy)ethoxychloroethane, etc., in the presence of a solvent such as 50% aqueous ethanol, other aqueous alcohols such as methanol, propanol, etc., p-dioxane-water, tetrahydrofuran-water, dimethylformamide, dimethyl-sulfoxide, hexamethylphosphoric triamide and the like. In addition to the solvent, the reaction is generally carried out in the presence of at least six molar equivalents of a base such as sodium hydroxide, potassium hydroxide, ammonium hydroxide, sodium hydride, and the like. The reaction time, temperature, and concentration may be varied over a wide range; however, it is necessary to purge the reaction mixture with argon or other inert gases in order to prevent oxidative decomposition of the starting material which rapidly occurs in the presence of oxygen and base. The cyclotriveratrylene derivative useful in the production of the compounds of this invention is characterized by the following formula II:

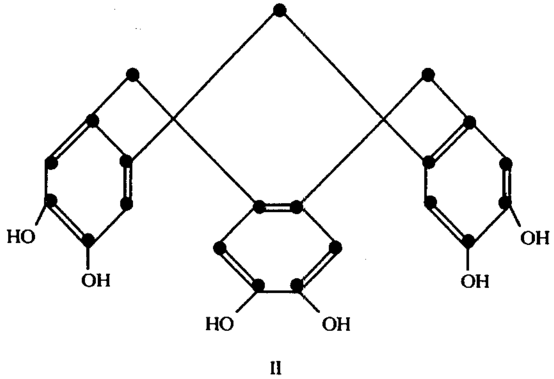

II

This compound may be prepared as disclosed by Lindsey (*J. Chem. Soc.* 1965, p. 1685-1691-92).

The compounds thus prepared are useful as complexing agents which solubilize usually insoluble inorganic compounds and salts of organic compounds in organic solvents. Examples include the solubilization by the compounds of this invention wherein R = $-(CH_2CH_2O)_2CH_2CH_3$ and R = $-(CH_2CH_2O)_3CH_2CH_3$ of sodium bromide, potassium bromide, sodium iodide, ammonium iodide, ammonium bromide and magnesium chloride in toluene-methanol, of sodium cyanide, potassium cyanide, and potassium acetate in acetonitrile, and of potassium carbonate in methylene chloride. The utility of such solutions in organic synthesis is well-known and is reviewed by Gokel and Durst in *Synthesis*, 1976, p-168-184. The following examples are set forth by way of illustration.

EXAMPLE 1

Preparation of Compound I (R = $-(CH_2CH_2-O)_2CH_2CH_3$)

A solution of 1.0 gram cyclotriveratrylene derivative II and 7.8 grams diethylene glycol monoethyl ether p-toluenesulfonate in 25 ml. 50% aqueous ethanol was purged with argon for 2.0 hours, and an argon-purged solution of 1.08 grams sodium hydroxide in 10 ml. 50% aqueous ethanol was added. The mixture was heated at reflux under argon 16 hours, and then stripped of solvent in vacuo. The residue was extracted with ether or methylene chloride to afford crude I (R = $-(CH_2CH_2-O)_2CH_2CH_3$) as an orange syrup which could be purified by chromatography on silica gel. Yield, 1.90 grams light yellow syrup.

EXAMPLE 2

Preparation of Compound I (R = $-(CH_2CH_2-O)_2CH_3$)

The procedure given in Example 1 was followed exactly, except that 7.48 grams diethylene glycol monomethyl ether p-toluenesulfonate was used instead of the diethylene glycol monoethyl ether p-toluene-sulfonate. Chromatography of the crude product afforded 2.50 grams I (R = $-(CH_2CH_2-O)-CH_3$) as a light yellow syrup.

EXAMPLE 3

Preparation of Compound I (R = $-(CH_2CH_2O)_3CH_2CH_3$)

A solution of 7.32 g. (0.02 mole) cyclotriveratrylene derivative I (R = H) in 100 ml dry dimethylformamide was treated with 53.3 g. (0.16 mole) triethyleneglycol monoethyl ethyl ether p-toluenesulfonate and stirred during argon purging for 4 hours. Sodium hydride, 3.36 g. (0.14 mole) was added to the reaction mixture over 1 hour, and the mixture stirred at 90° for 4 hours. The mixture was let stand overnight, the dimethylformamide distilled off in vacuo, and the semisolid residue diluted with 100 ml. methylene chloride, filtered, and the filtrate stripped of methylene chloride in vacuo. The residual crude product was purified by chromatography on silica gel to afford 11.0 g. I ($R = (CH_2CH_3-O)_3CH_2CH_3$) as a light yellow syrup.

EXAMPLE 4

Solubilization of KBr in Toluene-Methanol by I ($R = (CH_2CH_2-O)_2CH_2CH_3$)

A slurry of finely divided KBr was prepared by adding toluene to a warm solution of KBr in methanol until the KBr was precipitated. Compound I ($R = (CH_2CH_2-O)_2CH_2CH_3$ was then added to the suspension in an amount equimolar to that of KBr present, whereupon the KBr dissolved in the methanol-toluene mixture.

EXAMPLE 5

Preparation of Phenylacetonitrile from Benzyl Chloride Using I ($R = (CH_2CH_2O)_2CH_2CH_3$) as Catalyst A mixture of 0.635 g. (0.005 mole) benzyl chloride, 0.50 g. sodium cyanide (0.010 mole), 0.53 g. (0.0005 mole) compound I ($R = (CH_2CH_2-O)_2CH_2CH_3$), and 15 ml. acetonitrile was stirred at reflux for 3.0 hours, at which time vapor-phase chromatographic analysis of the reaction mixture showed complete consumption of benzyl chloride and formation of phenylacetonitrile as the sole product. The reaction mixture was poured into water and extracted with petroleum ether to afford phenylacetonitrile and recovered catalyst I (82% yield).

A control experiment in which the complexing agent I ($R = (CH_2CH_2-O)_2CH_2CH_3$) was omitted gave less than 5% conversion to phenylacetonitrile in 3.0 hours.

EXAMPLE 6

Preparation of Benzyl Acetate from Benzyl Chloride Using I ($R = (CH_2CH_2-O)_3CH_2CH_3$) as Catalyst A mixture of 1.27 g. (0.01 mole) benzyl chloride, 1.64 g. (0.02 mole) dry sodium acetate, 0.71 g. (0.0005 mole) compound I ($R = (CH_2CH_2-O)_3CH_2CH_3$), and 15 ml. acetonitrile was stirred at reflux for 12 hours Analysis of the reaction mixture disclosed conversion of benzyl chloride to benzyl acetate; the catalytic quantity of compound I was unchanged. A control reaction run in the absence of compound I failed to produce benzyl acetate.

EXAMPLE 7

Use of Compound I ($R = (CH_2CH_2-O)_3CH_2CH_3$) to Catalyze A Wittig Reaction A reaction mixture composed of compound I ($R = (CH_2CH_2-O)_3CH_2CH_3$), 0.40 g. (0.003 mole), benzyltriphenylphosphonium chloride, 1.2 g. (.003 mole), benzaldehyde, 0.33 g. (.003 mole), potassium carbonate, 1.5 g., and 15 ml. dichloromethane was stirred at reflux for 2 hours. Analysis of the mixture at this point disclosed consumption of the benzaldehyde and benzyltriphenylphosphonium chloride and formation of 1,2-diphenyl-ethylene (1:1 mixture of cis and trans) in about 90% yield.

The invention has been described in detail with particular reference to preferred embodiments thereof, but it will be understood that variations and modifications can be effected within the spirit and scope of the invention.

I claim:

1. A compound having the formula

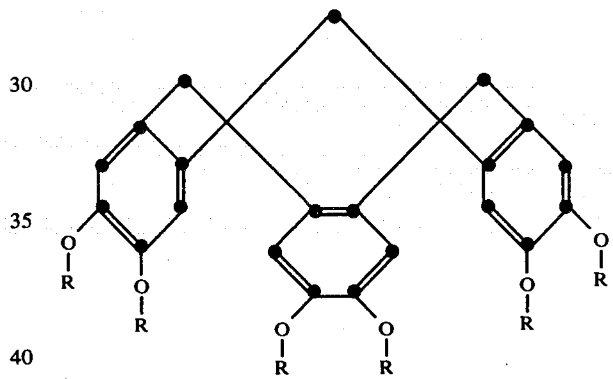

wherein R is $(CH_2-CH_2-O)_nR^1$, $n$ is an integer of 1 to 5 and $R^1$ is alkyl having 1 to 6 carbon atoms.

2. Compound according to claim 1 wherein $n$ is 2 and $R^1$ is methyl.

3. Compound according to claim 1 wherein $n$ is 2 and $R^1$ is ethyl.

4. Compound according to claim 1 wherein $n$ is 3 and $R^1$ is ethyl.

5. Compound according to claim 1 wherein $n$ is 4 and $R^1$ is methyl.

* * * * *